United States Patent

Omori

Patent Number: 5,993,442
Date of Patent: Nov. 30, 1999

[54] MEDICAL LASER IRRADIATION APPARATUS

[75] Inventor: Shigeru Omori, Nakai-machi, Japan

[73] Assignee: Termuno Kabushiki Kaisha, Tokyo, Japan

[21] Appl. No.: 09/046,586

[22] Filed: Mar. 24, 1998

[30] Foreign Application Priority Data

Mar. 25, 1997 [JP] Japan .................................. 9-072384

[51] Int. Cl.⁶ .................................................. A61B 17/36
[52] U.S. Cl. ................................ 606/10; 606/16; 606/17
[58] Field of Search ............................. 606/2, 3, 10, 11, 606/12, 13, 14, 15, 16, 17

[56] References Cited

U.S. PATENT DOCUMENTS

| | | | |
|---|---|---|---|
| 3,821,510 | 6/1974 | Muncheryan | 606/16 X |
| 4,580,557 | 4/1986 | Hertzmann | 606/12 |
| 4,852,567 | 8/1989 | Sinofsky | 606/3 |
| 5,150,704 | 9/1992 | Tatebayashi et al. | 606/10 |
| 5,460,182 | 10/1995 | Goodman et al. | 606/2 |
| 5,468,238 | 11/1995 | Mersch | 606/15 |
| 5,500,918 | 3/1996 | Pileski et al. | 606/16 |
| 5,568,503 | 10/1996 | Omori | 372/70 |
| 5,873,875 | 2/1999 | Altshuler | 606/10 |
| 5,879,376 | 3/1999 | Miller | 606/9 |

FOREIGN PATENT DOCUMENTS

| | | |
|---|---|---|
| 1-167812 | 7/1989 | Japan . |
| 6-233778 | 8/1994 | Japan . |
| 7-106665 | 4/1995 | Japan . |
| 9-129949 | 5/1997 | Japan . |

Primary Examiner—Michael Peffley
Assistant Examiner—Soya Harris Ogugua
Attorney, Agent, or Firm—Burns, Doane, Swecker & Mathis, LLP

[57] ABSTRACT

The present invention is for the purpose of providing a medical laser irradiation apparatus which applies laser beams of two or more wavelengths, incapable of transmitting in a quartz optical fiber, through the use of an optical fiber cable, with this medical laser irradiation apparatus being easy to handle and producible at a low cost, and also capable of making irradiation through the use of a relay optical fiber cable comprising a quartz optical fiber. For this purpose, this apparatus is composed of a laser irradiation apparatus to output laser beams of a plurality of wavelengths capable of being transmitted by a quartz optical fiber, and two or more kinds of irradiation optical fiber cables including an optical fiber cable having a quartz optical fiber and containing a solid state laser medium and/or a nonlinear optical crystal at its tip portion. Thus, by using properly the plurality of irradiation optical fiber cables, it is possible to apply laser beams of two or more kinds of wavelengths, incapable of being transmitted by a quartz optical fiber, to an appropriate place through the use of one small-sized laser generating means.

11 Claims, 12 Drawing Sheets

MEDICAL LASER IRRADIATION APPARATUS

BACKGROUND OF THE INVENTION

The present invention relates to diagnostic and treating equipment in the medical field, and more particularly to a medical laser irradiation apparatus suitably used for displaying different effects through the use of a plurality of laser wavelengths.

RELATED ART

In the case of employing a laser beam (light) for medical applications, since the effects on organic tissues vary in accordance with the wavelength of the laser beam, in general, a laser device capable of outputting a laser wavelength answering the purpose is selected. For instance, in the case of solidifying an organic tissue for medical purpose, a laser beam in a range from a visible region to a near infrared region, which shows a relatively deep penetration property, is suitable. While in the case of evaporating an organic tissues, a laser beam in an infrared region, which shows shallow penetration property, is more effective. Further, for observing a fluorescence for a medical purpose, a laser beam in an ultraviolet region is appropriate.

In a medical laser irradiation apparatus, a laser guiding means such as an optical fiber may be coupled to an apparatus equipped with at least one laser oscillator to guide a laser beam to a given place. In the case of irradiating with laser beams with two or more wavelengths, the laser irradiation apparatus is provided with laser oscillators corresponding to different wavelengths, and if at least one of the laser wavelengths is within an ultraviolet region below 300 nm or within an infrared region above 2.5 $\mu$m, as the laser guiding means, in addition to a general-purpose quartz optical fiber, an ultraviolet or infrared dedicated optical fiber may be used.

Figure 9:
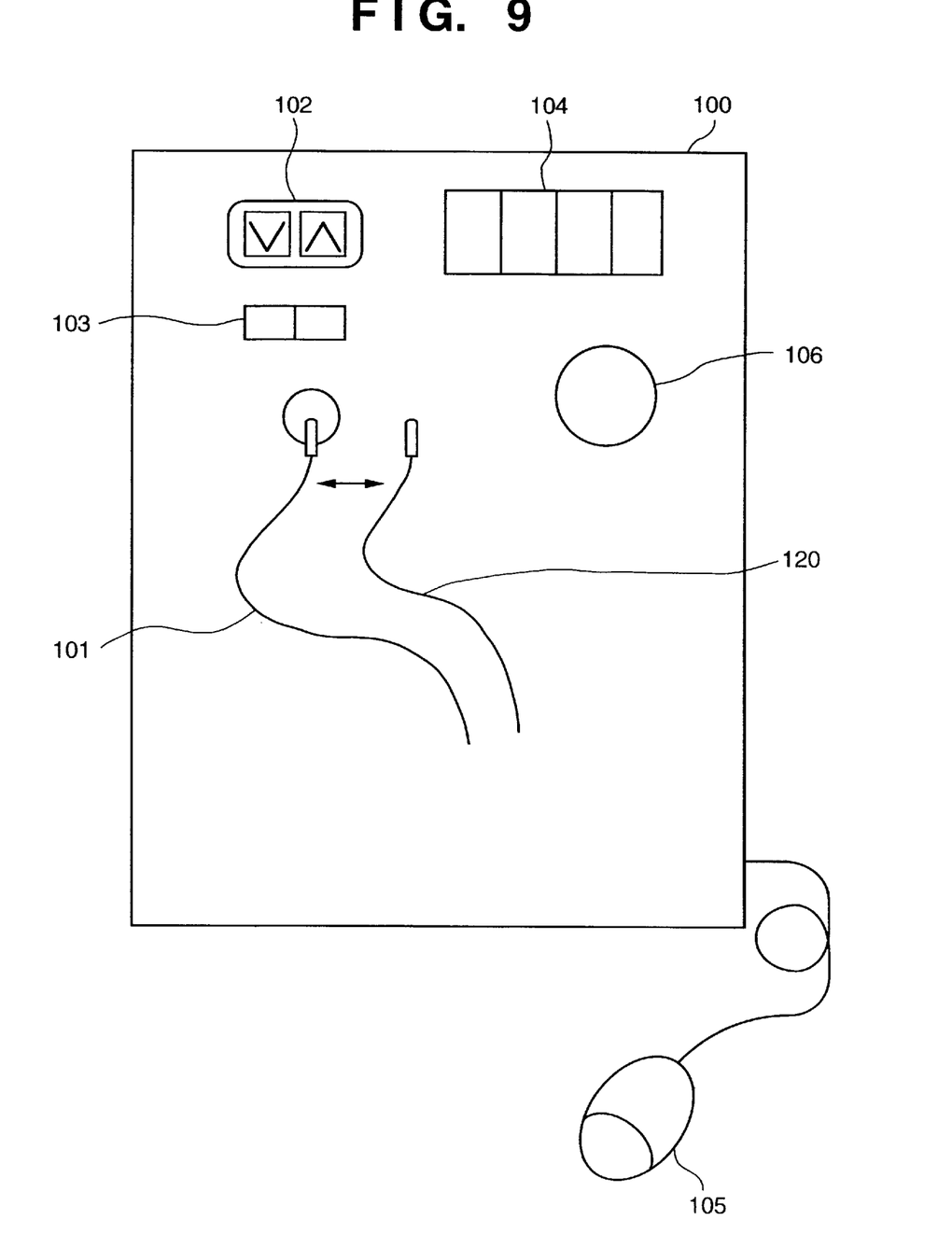
FIG. 9 is an illustration of an appearance of a medical laser irradiation apparatus.

FIG. 9 is an illustration of one example of an arrangement serving as medical laser irradiation apparatus for making laser beam irradiation having two or more wavelengths as mentioned above, which was devised by this inventor at the same time. In FIG. 9, numeral 100 represents a laser irradiation apparatus, 101 designates a quartz optical fiber, numeral 120 denotes a fluoride optical fiber, numeral 102 depicts an output setting switch, numeral 103 stands for a laser wavelength selector switch, numeral 104 signifies a display for displaying the output power or a set irradiation time, numeral 105 indicates a foot switch for performing a laser irradiation, and numeral 106 shows an emergency shutdown (safety) switch. Further, FIG. 10 exemplifies an internal construction of the FIG. 9 medical laser irradiation apparatus, and in FIG. 10, numeral 110 represents an Nd:YAG laser serving as a first laser oscillating section for outputting a laser beam 111 with a first wavelength of 1.064 $\mu$m, numeral 112 designates an Er:YAG laser acting as a second laser oscillating section for outputting a laser beam 113 with a second wavelength of 2.94 $\mu$m, numeral 114 denotes a fixed reflecting mirror, numeral 115 depicts a movable reflecting mirror, and numeral 116 signifies a focusing lens.

Figure 10:
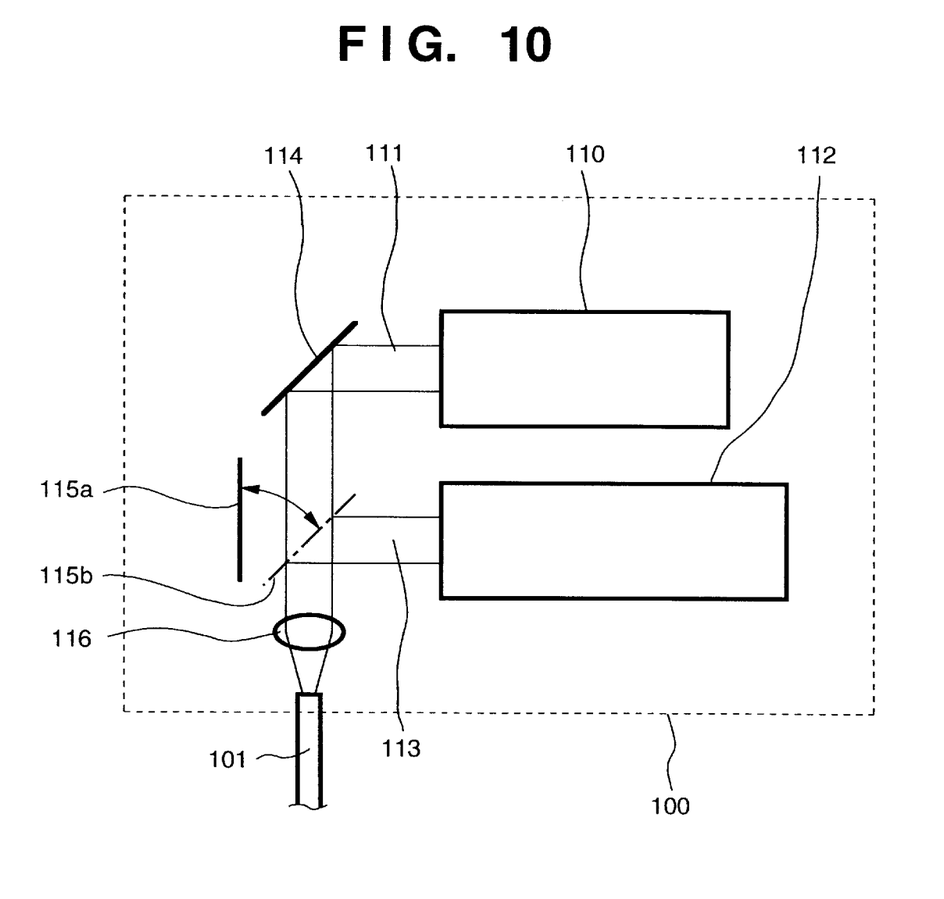
FIG. 10 is an illustration of an internal construction of the medical laser irradiation apparatus.

A description will be made hereinbelow of the medical laser irradiation apparatus thus arranged. First, through the use of the this apparatus, for emitting the laser beam 111 with the wavelength of 1.064 $\mu$m from the tip portion of the optical fiber 101, the laser oscillating section 110 is chosen through the wavelength selector switch 103 so that the movable reflecting mirror 115 is put at a position expressed at numeral 115a and the laser oscillating section 110 assumes a waiting condition.

Next, the operator steps on the foot switch 105 to put the laser oscillating section 110 into operation, thereby emitting the laser beam 111 with the wavelength of 1.064 $\mu$m. The laser beam 111 is reflected by the fixed reflecting mirror 114 to a different optical path to be incident on the focusing lens 116 and then incident on the optical fiber 101 to be transmitted to the tip portion of the optical fiber 101 and applied onto the irradiation place.

For emitting of a laser beam with a wavelength of 2.94 $\mu$m, the light-guiding optical fiber is replaced with the fluoride optical fiber 120, and the laser oscillating section 112 is chosen through the wavelength selector switch 103 so that the movable reflecting mirror 115 is put at a position designated at numeral 115b and the laser oscillating section 112 goes into a waiting condition. Subsequently, the foot switch 105 is stepped on so that the laser oscillating section 112 begins oscillation. The laser beam 113 with the wavelength of 2.94 $\mu$m outputted from the laser oscillating section 112 undergoes the optical path change due to the movable reflecting mirror 115 to be incident on the focusing lens 116 and further incident on the optical fiber 101 to be transmitted to the tip portion of the optical fiber 101 and applied onto the irradiation place.

Moreover, as another means for making an irradiation of a laser beam, whose wavelength is within an ultraviolet region below 300 nm or within an infrared region above 2.5 $\mu$m, from an optical fiber tip, there has been proposed an apparatus containing a nonlinear optical crystal and/or a solid state laser medium in an optical fiber tip portion, which is disclosed in Japanese Provisional Publication Nos. 1-167812, 7-106665 and 9-129949.

However, according to a study by this inventor and others, in the medical laser irradiation apparatus based upon the above-mentioned constructions, in the case of emitting a laser beam from an optical fiber the laser beams of a plurality of wavelengths included as the irradiation laser wavelengths within an ultraviolet region below 300 nm or within an infrared region above 2.5 $\mu$m, a plurality of laser oscillating sections capable of outputting the aforesaid laser wavelengths are required to be provided within the apparatus, so that the apparatus becomes considerably bulky and costly. Further, a special-purpose optical fiber is needed in addition to the general-purpose quartz optical fiber.

In addition, in the case of such laser irradiation apparatus, in general, when a light-guiding optical fiber is inserted into the interior of a living body together with a different medical device such as a catheter, if length of the light-guiding optical fiber is extremely longer than the length of the different medical device, this is undesirable from the viewpoint of operation or treatment such as sterilization. In the above-mentioned laser irradiation apparatus, when switching the irradiation laser wavelength, since it is necessary that the light-guiding optical fiber be once detached from the connection section of the apparatus and replaced with a different one corresponding to the wavelength, the length of the light-guiding optical fiber must extend from the apparatus up to the laser irradiation target, and hence, becomes extremely longer when compared with the different medical device extending from the target place to the vicinity of the user outside the living body. This creates a serious problem in practical use.

Furthermore, in the case of the aforesaid prior art containing a nonlinear optical crystal and/or a solid state laser medium in an optical fiber tip portion, each optimal wavelength laser source must be provided with a laser irradiation apparatus for the excitation of the solid laser medium and/or the wavelength conversion by the nonlinear optical element, and there is no interchangeability between the laser irradiation apparatus and the optical fiber cable containing the nonlinear optical crystal and/or the solid state laser medium. Thus, there is a problem in that it is necessary that the laser irradiation apparatus and the optical fiber cable be paired for every output laser wavelength.

SUMMARY OF THE INVENTION

Accordingly, the present invention has been developed to eliminating the foregoing problems, and it is an object of this invention to provide a medical laser irradiation apparatus which is capable of conveniently supplying laser beams with two or more kinds of wavelengths including a wavelength in an ultraviolet region below 300 nm or in an infrared region above 2.5 $\mu$m through the use of one apparatus.

For eliminating the aforesaid problems and achieving the purpose, a laser irradiation apparatus according to this invention features the following arrangement.

In a medical laser irradiation apparatus including a laser irradiation apparatus and at least two irradiation optical fiber cables coupled to the laser irradiation apparatus; the irradiation optical fiber cables comprise quartz optical fibers used as light guiding paths, and a solid state laser medium and/or a nonlinear optical crystal capable of generating a laser beam with a wavelength which is substantially difficult to guide through the quartz optical fibers are set on tip portions of the quartz optical fibers; and the laser irradiation apparatus is equipped with laser generating means capable of generating laser beams of a plurality of wavelengths which are transmittable through the quartz optical fibers and a laser beam emitting opening. Thus, in accordance with the kinds of irradiation optical fiber cables connected to the laser irradiation apparatus, a laser beam with a wavelength suitable for the excitation of the solid state laser medium or for a wavelength conversion by the nonlinear optical crystal is selectively guided through the interiors of the irradiation optical fiber cables, and the laser beams of at least two wavelengths which can not be guided through the quartz optical fibers are emitted from the tip portions of the irradiation optical fiber cables.

Other objects and advantages besides those discussed above shall be apparent to those skilled in the art from the description of a preferred embodiment of the invention which follows. In the description, reference is made to accompanying drawings, which form a part thereof, and which illustrate an example of the invention. Such example, however, is not exhaustive of the various embodiments of the invention, and therefore reference is made to the claims which follow the description for determining the scope of the invention.

DETAILED DESCRIPTION OF THE PREFERRED EMBODIMENTS

Referring to the accompanying drawings, a detailed description will be made hereinbelow of preferred embodiments of laser irradiation apparatus according to the present invention.

In a laser irradiation apparatus according to an embodiment of this invention, when, for example, an irradiation optical fiber cable having, at its tip portion a nonlinear optical crystal capable of outputting a laser beam whose wavelength is below 300 nm, an irradiation optical fiber cable having, at its tip portion, a solid state laser medium capable of outputting a laser beam whose wavelength is above 2.5 $\mu$m, or an irradiation optical fiber cable comprising a quartz optical fiber are coupled to a laser irradiation apparatus, the laser beam led through the irradiation optical fiber cable is switched to have a wavelength suitable in accordance with the kind of the irradiation optical fiber cable, and a laser beam with a wavelength below 300 nm or above 2.5 $\mu$m or a diode laser beam with a near infrared wavelength suitable as a laser light source for the laser irradiation apparatus can be emitted from the different irradiation optical fiber cable tip portions.

Thus, by only selecting the kind of the irradiation optical fiber cable to be used, laser beams of a plurality of wavelengths including a laser beam in a wavelength region failing to effectively transmit (to be guided) through a quartz optical fiber can be emitted from the irradiation optical fiber cable tip portion through one small-sized medical laser irradiation apparatus. It becomes possible to perform the diagnosis using an ultraviolet laser beam, the solidification using a near infrared laser beam and the transpiration using an infrared laser beam. In addition, since all the irradiation optical fiber cables have a quartz optical fiber as a light guiding path, a relay optical fiber cable comprising a quartz optical fiber is insertable into between the irradiation optical fiber cable and the laser irradiation apparatus. This can shorten the length of the irradiation optical fiber cable up to a value less than the distance from the laser irradiation apparatus to the place subjected to the irradiation, thus setting the length thereof a different medical device to be used together with the laser apparatus.

Furthermore, a means to detect the type of each optical fiber cable is placed at the connection section between two or more irradiation optical fiber cables and the laser irradiation apparatus or the relay optical fiber cable. The result is that the necessary laser beam can be safely emitted without connecting an irradiation optical fiber cable in error.

Figure 1:
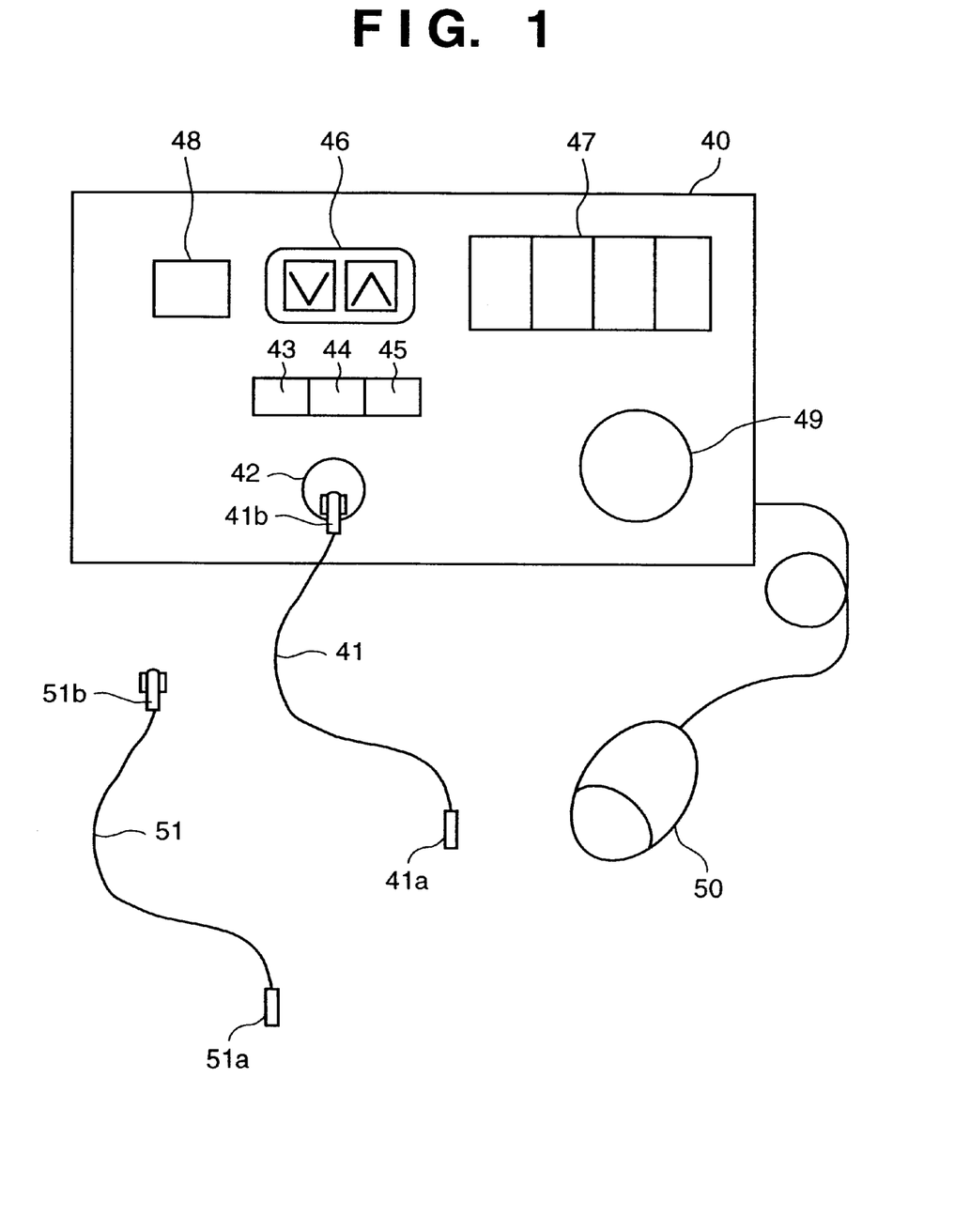
FIG. 1 is an illustration of an arrangement of a medical laser irradiation apparatus according to a first embodiment of the present invention.

FIG. 1 is an illustration of an arrangement of a medical laser irradiation apparatus according to a first embodiment of this invention, which can emit a laser beam with a wavelength assuming any one of 970 nm, 2.8 µm or 275.5 nm by reconnecting three kinds of irradiation optical fiber cables.

In FIG. 1, numeral 40 represents a laser irradiation apparatus internally including a diode laser light source for a wavelength of 970 nm and a control circuit for taking the charge of the lighting control of the diode laser. In addition, it contains a temperature control unit capable of adjusting the wavelength in a range of 10 nm by changing or altering the temperature of the diode laser light source.

Figure 2:
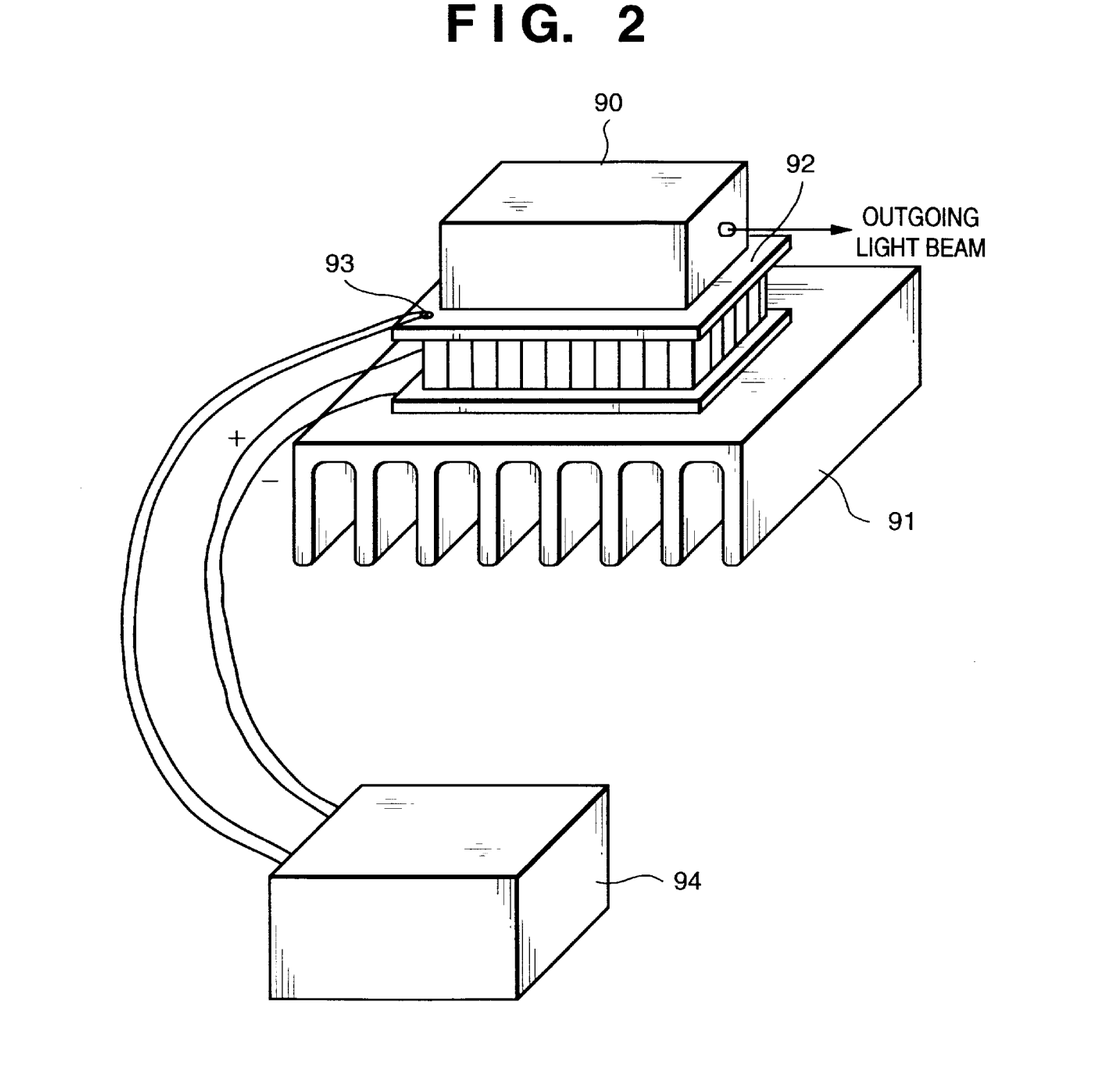
FIG. 2 is an illustration of an arrangement for controlling the temperature of a diode laser light source.

As shown in FIG. 2, the aforesaid diode laser light source, designated at numeral 90, is mounted on a Peltier device 92 equipped with the radiation fins 91. The Peltier device 92 is made to vary the quantity of heat generated in response to a given current value, and the heat generated by this Peltier device 92 heats or cools the diode laser light source 90. The Peltier device 92 is provided with a temperature monitoring thermister 93. The temperature monitored by this thermister 93 is feedbacked to a temperature control unit 94 which internally include a driver circuit for the Peltier device 92 to control the temperature of the Peltier device 92, thus, the diode laser light source 90. The diode laser light source 90 is made, for example, so that the wavelength of a laser beam outputted varies by 0.3 nm when the temperature varies by 1° C., and when the temperature variation of ±20° C. occurs, the wavelength of the laser beam outputted can vary by ±6 nm.

Numeral 41 denotes one of the irradiation optical fiber cables, and a solid state laser oscillating section capable of producing a light beam with a wavelength of 2.8 µm is integrally attached to a tip portion 41a of a quartz optical fiber, while the other end portion is equipped with a connector 41b for connection with a laser irradiation apparatus 40. The connector 41b has a projection which identify the irradiation optical fiber cable 41. Numeral 51 depicts a different one of the irradiation optical fiber cables, and a solid state laser medium capable of generating a laser beam with a wavelength of 551 nm and a nonlinear optical crystal are integrally provided at a tip portion 51a of a quartz fiber, whereas the other end portion is equipped with a connector 51b for establishing a connection with the laser irradiation apparatus 40. On the connector 51b, includes a projection which can identify the irradiation optical fiber cable 51. Numeral 42 signifies a receptacle for making a connection of any one of the aforesaid three kinds of irradiation optical fiber cables in the laser irradiation apparatus 40, which has a mechanism to detect the fiber type identifying projection in the connector 41b at the connection of the irradiation optical fiber cable.

Numerals 43, 44 and 45 designate indicators for indicating the connected one of the aforesaid three kinds of irradiation optical fiber cables on the basis of an identification signal from the detection mechanism. Of these indicators, the indicator 44 corresponds to the irradiation optical fiber cable having, at its tip portion, the solid state laser oscillating section capable of generating the laser beam with a wavelength of 2.8 µm. The indicator 44 is for the irradiation optical fiber cable having, at its tip portion, the solid state laser medium capable of generating a laser beam with a wavelength of 551 nm and a wavelength converting device comprising a nonlinear optical crystal. The indicator 45 is for the irradiation optical fiber cable comprising a quartz optical fiber.

Numeral 48 denotes a switch and lamp device for indicating the allowance of the laser irradiation. Numeral 46 depicts an output setting switch for selecting the laser output level and an irradiation waveform. Numeral 47 signifies a display section for displaying the contents set through the setting switch 46. Numeral 50 represents a foot switch for the ON/OFF control of the laser output. Numeral 49 designates an emergency shutdown switch, with all operation stopping when depressing this switch 49.

Figure 3:
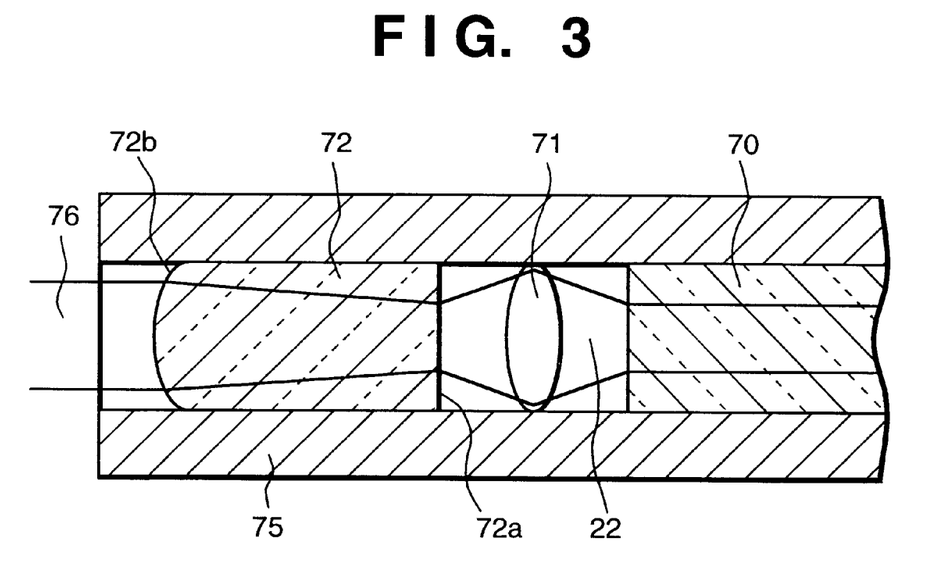
FIG. 3 is a cross-sectional view showing a principal portion of an irradiation optical fiber cable used for the medical laser irradiation apparatus according to the first embodiment of this invention.

FIG. 3 is an illustration of a cross section of the tip portion 41a of the irradiation optical fiber cable 41. In FIG. 3, numeral 70 represents a quartz optical fiber, numeral 22 denotes a diode laser beam whose wavelength is 967 nm. Numeral 71 designates a focusing lens of the diode laser beam 22, and numeral 72 depicts a YSGG crystal where Er is doped by 30% as a solid state laser medium capable of generating a laser beam with a wavelength of 2.8 µm. A reflecting mirror for laser with a wavelength of 2.8 µm being coated on each of an incidence plane 72a and an outgoing plane 72b, and the incidence plane 72a and the outgoing plane 72b comprises a laser resonator. Further, numeral 75 represents a sleeve for fixedly positioning the optical fiber 70, the focusing lens 71 and the solid state laser medium 72, and numeral 76 stands for an output laser beam whose wavelength is 2.8 µm.

Figure 4:
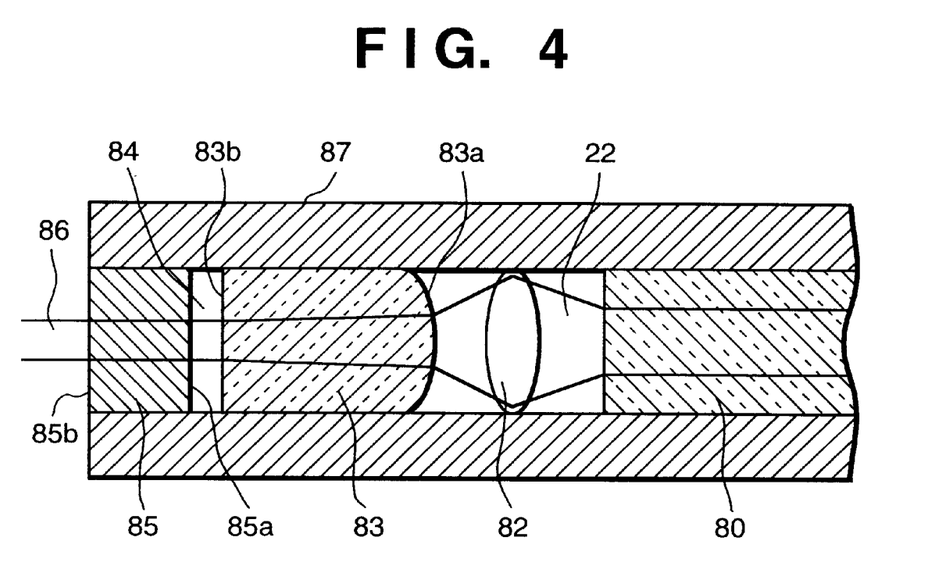
FIG. 4 is a cross-sectional view showing a principal portion of an irradiation optical fiber cable used for the medical laser irradiation apparatus according to the first embodiment of this invention.

FIG. 4 is an illustration of the tip portion of the irradiation optical fiber cable 51. In FIG. 4, numeral 80 represents a quartz optical fiber, numeral 22 designates a diode laser beam with a wavelength of 975 nm, numeral 82 denotes a focusing lens for the diode laser beam 22, numeral 83 depicts a YLF crystal where Er is doped by 5% as a solid state laser medium capable of generating a laser beam with a wavelength of 551 nm. Numeral 85 signifies a $\beta$-$BaB_2O_4$ serving as a nonlinear optical crystal for converting the laser beam wavelength of 551 nm into a beam of 275.5 nm. A reflecting mirror coating for the laser beam with a wavelength of 551 nm being made on each of an end surface 83a of the solid state laser medium 83 and an end surface 85b of the nonlinear optical crystal 85 while a non-reflective coating for the laser beam with a wavelength of 551 nm being formed on each of an end surface 83b of the solid state laser medium 83 and an end surface 85a of the nonlinear optical crystal 85, and with the end surface 83a and the end surface 85b constituting a laser resonator. Further, numeral 87 depicts a sleeve for fixedly positioning the quartz optical fiber 80, the focusing lens 82, the solid state laser medium 83 and the nonlinear optical crystal 85, numeral 84 stands for a laser beam whose wavelength is 551 nm, and numeral 86 designates an output laser beam whose wavelength is 275.5 nm.

Figure 5:
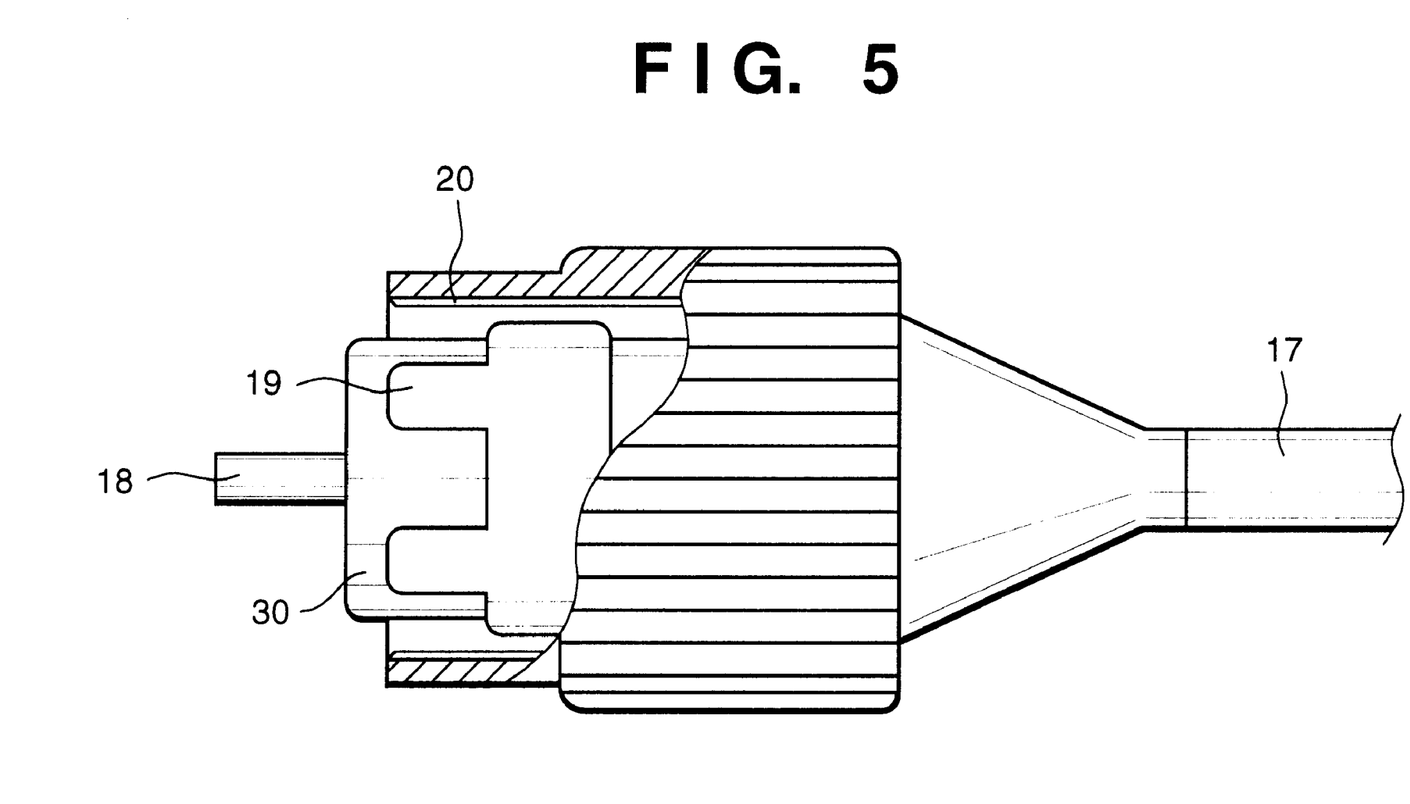
FIG. 5 is an illustration of a connection section of an irradiation optical fiber cable used for the medical laser irradiation apparatus according to the first embodiment of this invention.

FIG. 5 is an illustration of one example of structures of the connector 41b in FIG. 1. In FIG. 5, numeral 17 signifies an irradiation optical fiber cable, numeral 18 is a ferrule, and numeral 30 designates a fitting component for fixedly positioning the ferrule 18 at a central position and further for connecting it to the receptacle 42. Further, numeral 19 represents a projection section attached or formed integrally to or with the fitting component 30, with the projection section 19 having different configurations or assuming a given number of projections in accordance with the types of irradiation optical fiber cables in order to identify the different irradiation optical fiber cables. The receptacle 42 is equipped with a mechanism to detect the configurations of the projection section 19. Numeral 20 denotes a screw section for fixing the irradiation optical fiber cable to the laser irradiation apparatus 40.

Figure 6:
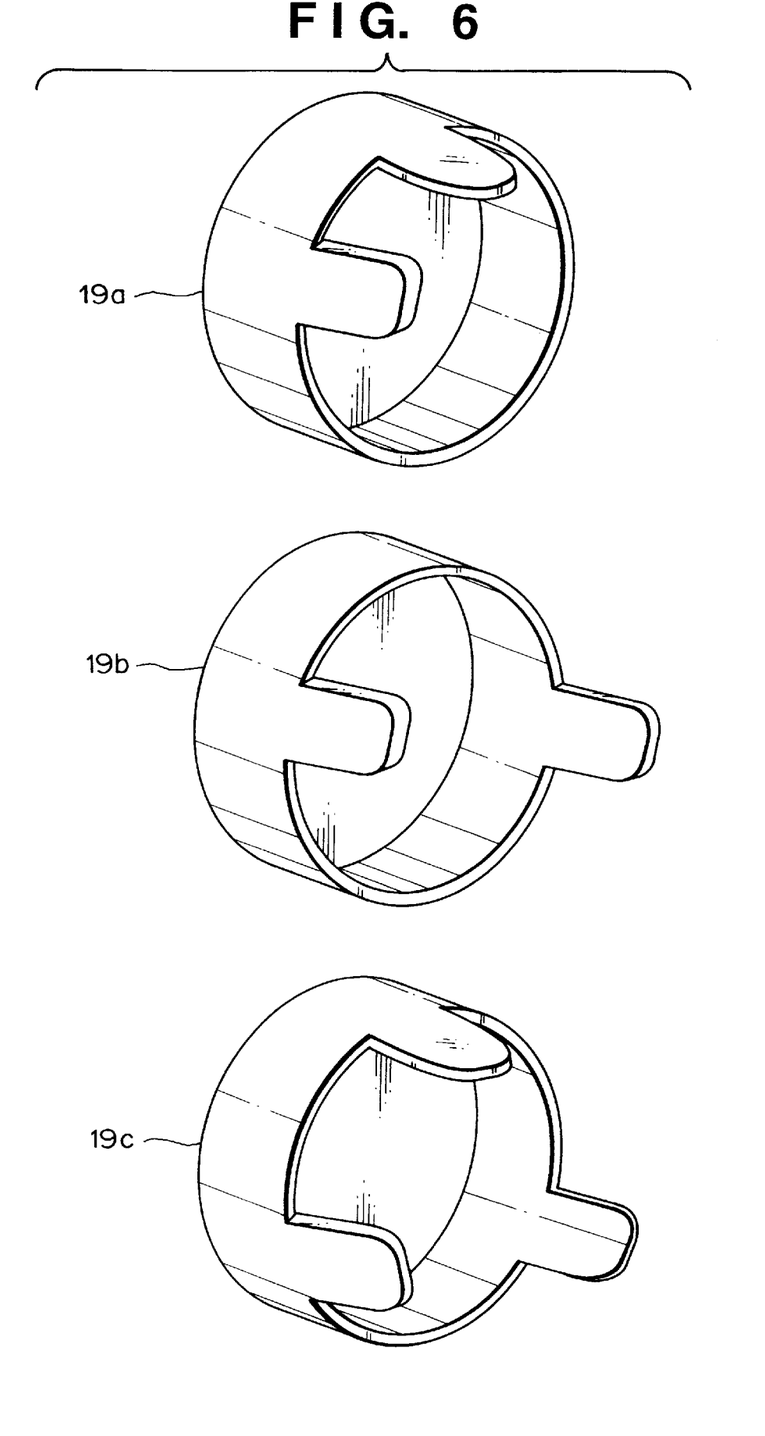
FIG. 6 is an illustration of parts used at the connection section of an irradiation optical fiber cable used for the medical laser irradiation apparatus according to the first embodiment of this invention.

FIG. 6 is an illustration of examples of configurations of the projections 19 for identifying three kinds of irradiation optical fiber cables, in the connect or exemplified in FIG. 5.

Figure 7:
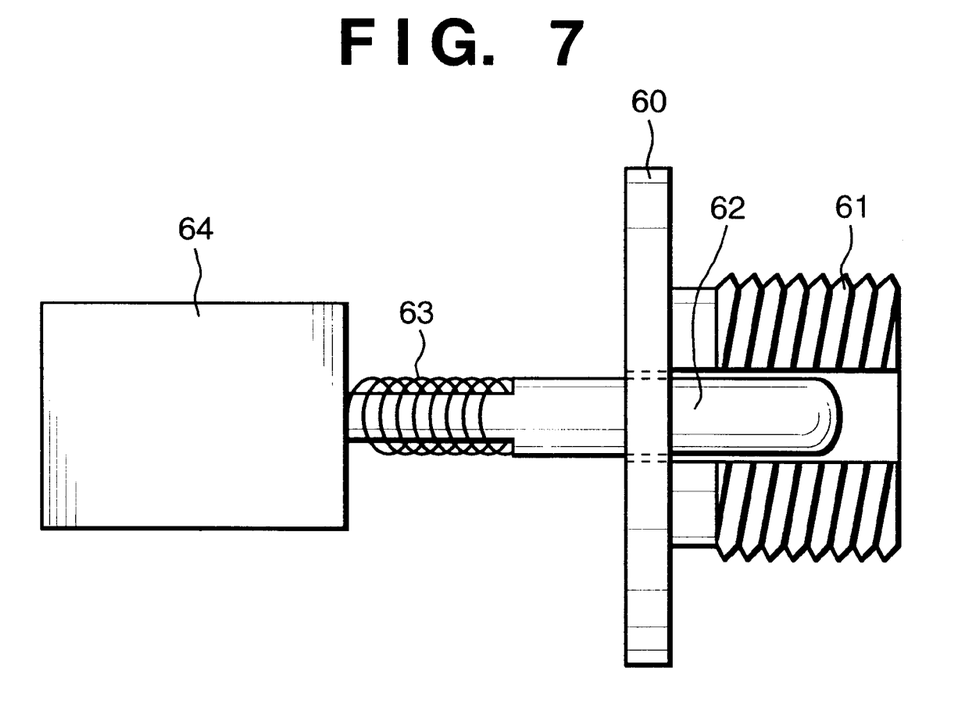
FIG. 7 is an illustration of a structure of an irradiation optical fiber cable connecting receptacle for the medical laser irradiation apparatus according to the first embodiment of this invention.

FIG. 7 is an illustration of one example of mechanisms for detecting the kinds of the irradiation optical fiber cables, in the receptacle 42 shown in FIG. 1. In FIG. 7, numeral 60 represents a receptacle body, numeral 61 is an irradiation optical fiber cable fixing screw section. Numeral 62 designates a slide section which shifts by depressing the FIG. 4 projection section 19 in the irradiation optical fiber cable connector and which is placed at a portion where the screw section 61 is partially cut off. Numeral 63 depicts a spring for pushing out the slide section 62 at a constant length, and numeral 64 denotes a switch which operates when the slide section 62 is pushed in by the connector projection section 19.

Referring to FIGS. 1 to 6, a description will be given hereinbelow of an operation of the medical laser irradiation apparatus constructed as described above.

As shown in FIG. 1, if the irradiation optical fiber cable 41 capable of emitting a laser beam with a wavelength of 2.8 $\mu$m is connected to the receptacle 42 in the laser irradiation apparatus 40, for example, the connector 41b has identifying projections such as a configuration indicated by numeral 19a in FIG. 5; the projection section 19a pushes down the corresponding portion of the slide section 62 (FIG. 7), the corresponding portion of the switch 64 turns ON; thereby detecting the connection of the irradiation optical fiber cable 41. Simultaneously with the ON state of the indicator 43, the temperature control unit 94 adjusts the temperature of the diode laser light source placed within the laser irradiation apparatus 40 to a temperature for generating a 967 nm laser beam which provides the highest efficiency when the solid state laser medium 72 produces a laser beam with a wavelength of 2.8 $\mu$m.

During laser irradiation by the irradiation optical fiber cable 41, the laser output mode, the output value and the irradiation time are set through the output setting switch 46 in FIG. 1 to appropriate values, and these values are displayed on the display section 47. In this case, the output mode signifies the modulation waveform of the irradiation laser beam intensity.

If the switch 48 is pressed after the completion of setting of the output setting switch 46, a lamp integral with this switch 48 goes on so that the aforesaid control circuit confirms no malfunction, thereafter going into a laser irradiation waiting condition. In this waiting condition, when the foot switch 50 in FIG. 1 is activated, a laser beam with a wavelength of 2.8 $\mu$m is outputted from the tip portion 41a of the irradiation optical fiber cable 41.

Since in the receptacle 42 the aforesaid slide sections are disposed at all the positions corresponding to the aforesaid identifying projections provided in the connector sections in accordance with the type of irradiation optical fiber cables, irradiation optical fiber cable is connectable to the receptacle 42 irrespective of its type, since the type of irradiation optical fiber cable can be automatically identified by means of the aforesaid detection mechanism. Accordingly, in the case of employing the irradiation optical fiber cable 51 with a solid state laser medium capable of generating a laser beam with a wavelength of 551 nm and the nonlinear optical crystal are provided integrally at the tip portion of the quartz optical fiber as shown in FIG. 4, for example, the identifying projection section in the connector section 51b to the FIG. 19b configuration in FIG. 6, the specific irradiation optical fiber cable 51 is determined through the receptacle 42. Concurrently with the turning on of indicator 44, the temperature control unit 94 alters the temperature of the diode laser light source provided within the laser irradiation apparatus 40 to a temperature for generating a 975 nm laser beam which provides the highest efficiency when the solid state laser medium 83 produces a laser beam whose wavelength is 551 nm.

During the irradiation by the irradiation optical fiber cable 51, the laser output mode, the output value and the irradiation time are set to appropriate values through the use of the output setting switch 46 in FIG. 1, and these values are displayed on the display section 47. On depressing the switch 48, after the completion of the setting of the output setting switch 46, a lamp integrated with this switch 48 lights, and after the aforesaid control circuit confirms that there is no malfunction, the laser irradiation waiting condition is entered. In this waiting condition, if the foot switch 50 in FIG. 1 is activated, a laser beam with a wavelength of 275.5 nm is outputted from the tip portion 51a of the irradiation optical fiber cable 51.

Furthermore, in a different operation of this laser irradiation apparatus, when using an irradiation optical fiber cable comprising a quartz optical fiber without any material at the tip porion, for example, if setting the identifying projection section in the aforesaid connector section to the 19c configuration shown in FIG. 5, the connection with the irradiation optical fiber cable is detected through the receptacle 42. Simultaneously with the indicator 45 going on, the wavelength of the diode laser light source placed within the laser irradiation apparatus 40 is altered to 970 nm.

During the irradiation by the irradiation optical fiber cable, the laser output mode, the output value and the irradiation time are set to appropriate values through the use of the output setting switch 46, and these values are displayed on the display section 47. If the switch 48 is depressed after the completion of the setting of the output setting switch 46, a lamp integrated with this switch 48 goes on, and after the aforesaid control circuit confirms that there is no malfunction, a laser irradiation ready condition is entered. In this ready condition, if the foot switch 50 is activated, a laser beam with a wavelength of 970 nm is emitted from the tip portion of the irradiation optical fiber cable. Needless to say, in the case of using the aforesaid irradiation optical fiber cable comprising only the quartz optical fiber, the wavelength of the diode laser light source 90 is variable by varying the temperature of the diode laser 90, for example, the selection thereof is possible in a range of 965 nm to 975 nm.

Figure 8:
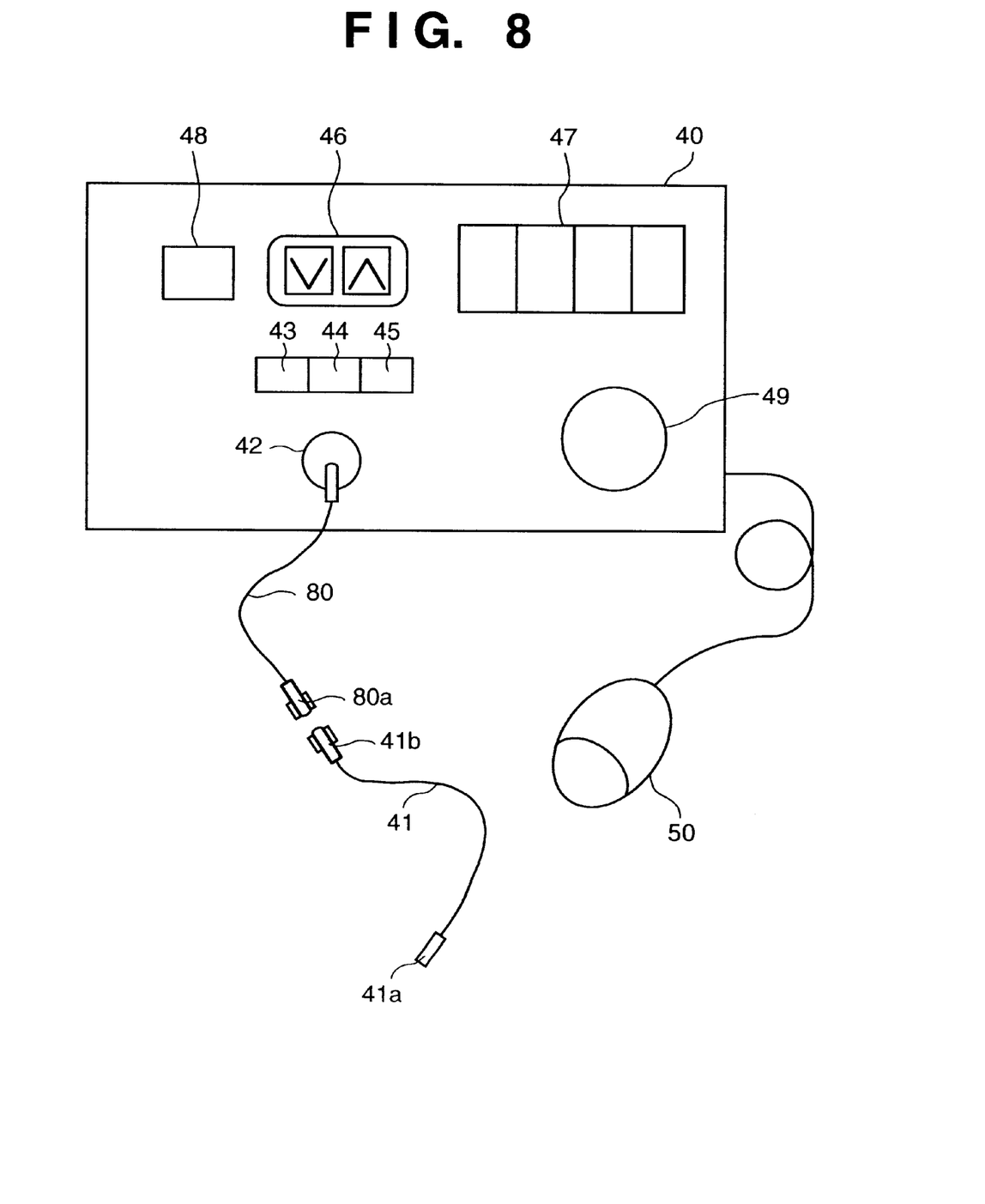
FIG. 8 is an illustration of an appearance of a medical laser irradiation apparatus according to a second embodiment of this invention.

FIG. 8 shows an arrangement of a medical laser irradiation apparatus according to a second embodiment of this invention. In FIG. 8, numeral 80 represents a relay optical fiber cable comprising a quartz optical fiber, and numeral 80a designates a receptacle which is positioned at the tip portion of the relay optical fiber cable 80 and which is equipped with a mechanism to detect the type of connection sections of irradiation optical fiber cables as shown in FIG. 7 and to relay this infomation to the laser irradiation apparatus 40, for example, by using an electric signal.

The operation of the medical laser irradiation apparatus according to the second embodiment constructed as mentioned above is basically similar to that of the above-described first embodiment, and the same components are marked with the same numerals and the description thereof will be omitted for brevity.

A feature of this embodiment is to employ the relay optical fiber cable 80, and all the three kinds of irradiation optical fiber cables mentioned in the first embodiment are made such that the quartz optical fiber is used as a light guiding path, they can be connected to the receptacle 80a at the tip portion of the relay optical fiber cable 80.

Furthermore, since the type of the irradiation optical fiber cable connected to the relay optical fiber cable 80 is detected by the receptacle 80a and the wavelength of a diode laser light source provided within the laser irradiation apparatus 40 is modified to an optimal value, the irradiation laser beam wavelength setting when using an irradiation optical fiber cable can be done in the same way as that of the first embodiment.

Naturally, the length of the irradiation optical fiber cable used in this embodiment can be shortened as compared with the first embodiment because of using the relay optical fiber cable between the laser irradiation apparatus and the irradiation optical fiber cable. Further, one relay optical fiber cable 80 is used therefore, laser beams of at least two wavelengths which can not transmit in a quartz optical fiber can be emitted from the tip portion of the irradiation optical fiber cable by replacing the type of the irradiation cable.

Incidentally, although in the above-described first and second embodiments one diode laser is used as the laser light source provided in the laser irradiation apparatus, other light sources are acceptable as long as they can generate a laser beam with a wavelength conforming to the type of the irradiation optical fiber cable to be connected to the laser irradiation apparatus, for instance, a wavelength variable laser such as a titanium-sapphire laser is suitable. In the case of employing a wavelength variable laser, it is also possible to use a laser in a band of 800 nm as a laser wavelength for transmitting in the irradiation optical fiber cable, and hence, in the above-described first and second embodiments, a cable having an Nd:YAG solid state laser crystal and two nonlinear optical crystals at its tip portion can be used as the aforesaid irradiation optical fiber cable capable of emitting an ultraviolet laser beam.

In addition, although the description of the above-described embodiments is that one laser light source is internally included in the laser irradiation apparatus, it is also appropriate to provide a plurality of laser light sources generating laser beams of a plurality of kinds of wavelengths.

Figure 11:
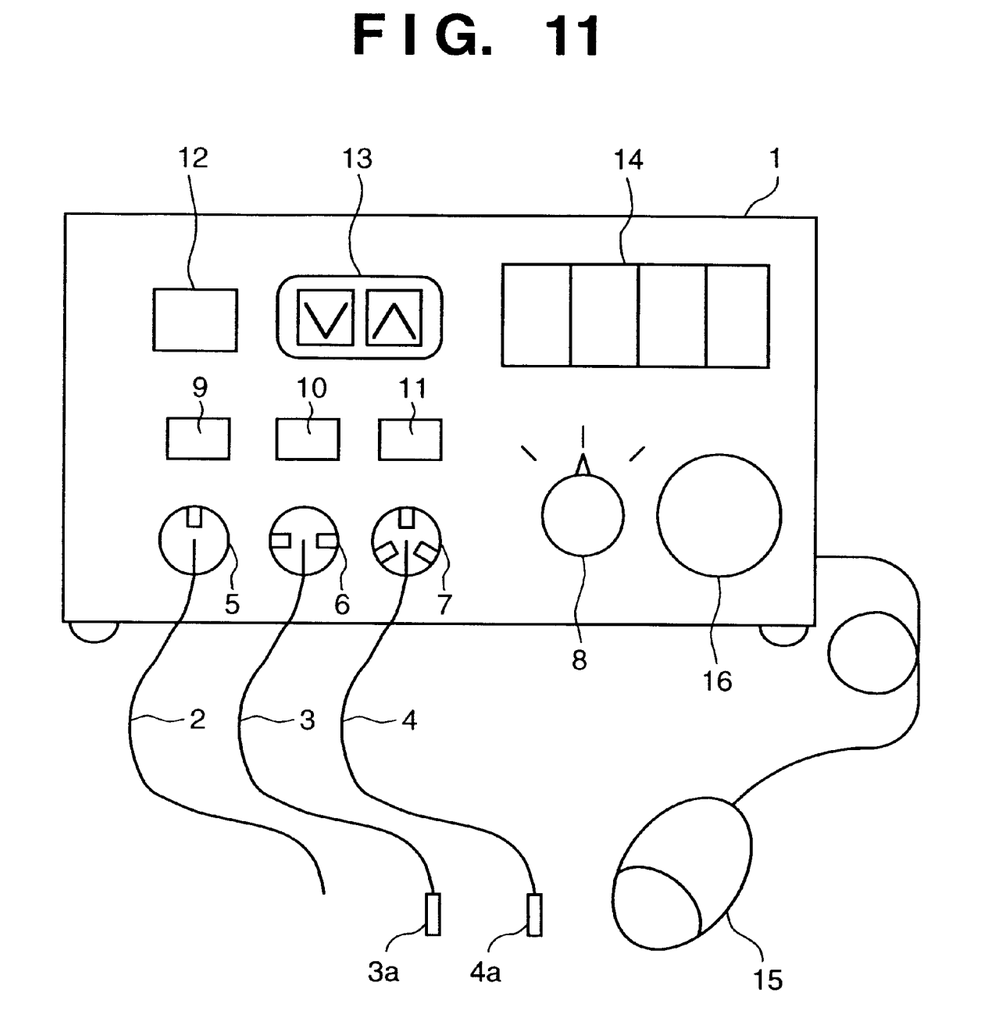
FIG. 11 is a schematic illustration of a medical laser irradiation apparatus according to a third embodiment of this invention.

FIG. 11 shows a medical laser irradiation apparatus according to a third embodiment of this invention. In FIG. 11, numeral 1 represents a laser irradiation apparatus which internally includes a diode laser light source for a wavelength of 970 nm. Further, numeral 2 designates a quartz optical fiber as a first optical fiber cable for irradiation, and numeral 3 denotes a second optical fiber cable for irradiation, with a solid state laser oscillating section capable of generating a laser beam with a wavelength of 2.8 μm is integrally placed at the tip portion 3a of a quartz optical fiber. Still further, numeral 4 depicts a third optical fiber cable for irradiation, with a solid state laser oscillating section capable of generating a laser beam with a wavelength of 551 nm and a wavelength converting section are integrally located at the tip portion 4a of a quartz optical fiber.

Numerals 5, 6 and 7 signify receptacles for the connection of the optical fiber cables 2, 3 and 4, respectively, in the laser irradiation apparatus, the receptacles being equipped with fitting sections having different configurations and with means to present erroneous combinations from being used, described herein later. Numeral 8 represents a selection switch for the optical fiber cables 2, 3, 4, and numerals 9, 10, 11 designate light-emitting lamp type indicators for indicating the optical fiber cables 2, 3, 4 selected through the selection switch 8.

Numeral 12 denotes a lamp and switch device for indicating the allowance of the laser irradiation, numeral 13 depicts an output setting switch for selecting the laser output and the modulation waveform, and numeral 14 signifies a display section for displaying the value set by the setting switch 13. Further, numeral 15 represents a foot switch which activates the laser to provide an output at an arbitrary timing when the operator steps on the switch. Still further, numeral 16 represents an emergency shutdown switch, where all operations stop in response to the depression of the switch 16.

The solid state laser oscillating section is integrally placed at the tip portion of the optical fiber cable 3 as mentioned before. Its structure is the same as that of the structure of the tip portion 41a of the irradiation optical fiber cable 41 in the first embodiment shown in FIG. 3.

Furthermore, the solid state laser oscillating section and the wavelength converting section comprising a nonlinear optical crystal integrally located at the tip portion of the optical fiber cable 4. The structure is the same as the structure of the tip portion 51a of the irradiation optical fiber cable 51 in the first embodiment shown in FIG. 4.

Still further, the structures of the connection sections of the optical fiber cables 2, 3, 4 to be fitted in the receptacles 5, 6, 7 in FIG. 11 are the same as that in the first embodiment shown in FIG. 5.

Moreover, the configurations of the projection section 19 for identifying the optical fiber cables 2, 3, 4 are also the same as those in the first embodiment shown in FIG. 6.

Figure 12:
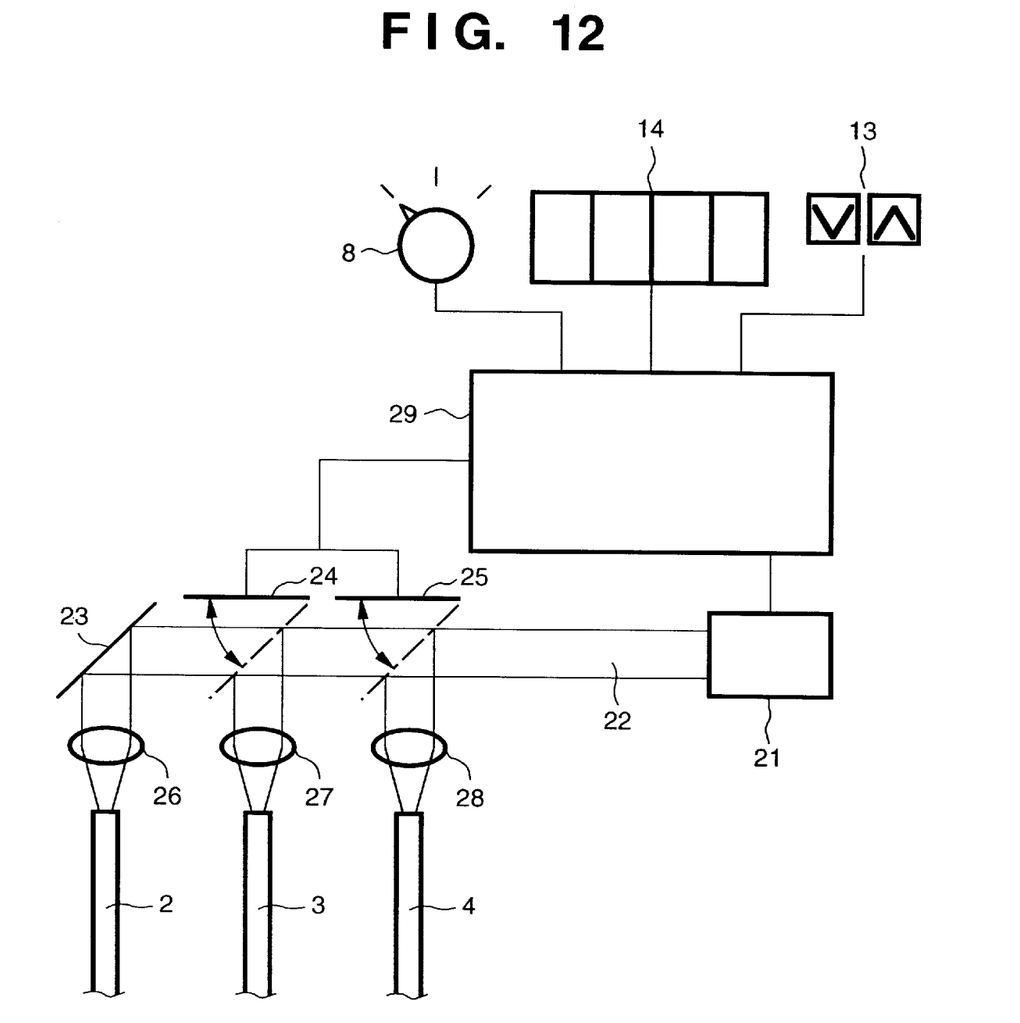
FIG. 12 is an illustration of a structure for changing the optical path of a laser beam.

FIG. 12 shows a mechanism for switching the laser beam to the optical cables for use in the interior of the laser irradiation apparatus 1. In FIG. 12, numeral 21 is a diode laser light source, numeral 22 designates a laser beam generated from the diode laser light source 21. Numerals 23, 24, 25 denote reflecting mirrors, and of these reflecting mirrors, the mirrors 24, 25 are equipped with a moving means. Numerals 26, 27, 28 depict focusing lenses for condensing the laser beam 22 reflected on the reflecting mirrors 23, 24, 25 to focus them on the optical fiber cables 2, 3, 4. Numeral 29 signifies a control circuit which controls the position of the reflecting mirror 24 or 25 in accordance with the kind of the optical fiber cable selected through the optical fiber cable selection switch 8 to switch the optical path of the laser beam 22, and further controls the temperature of the diode laser 21 to perform the wavelength adjustment when necessary. In addition, the control circuit 29 receives the input from the output setting switch 13 and controls the driving condition of the diode laser 21 to generate the laser output or the irradiation waveform displayed on the display section 14.

An operation of the medical laser irradiation apparatus thus arranged will be described hereinbelow with reference to FIGS. 11 and 12. For example, if setting the optical fiber cable selection switch 8 in FIG. 11 to the optical fiber 2, the lamp of the indicator 9 goes on and the reflecting mirrors 24, 25 move out of the optical path of the laser beam 22, and the laser beam 22 comes incident on the reflecting mirror 23 so that the optical path selection for the laser beam 22 is uses the optical fiber cable 2.

During the irradiation by the optical fiber cable 2, the laser output mode, the output value and the irradiation time are set to appropriate values through the use of the output setting switch 13, and these values are displayed on the display section 14. In this case, the output mode means the modulation waveform of the irradiation laser beam intensity.

If the switch 12 is pushed down after the completion of the setting of the optical fiber cable selection switch 8 and the output setting switch 13, the lamp integrated with the switch 12 lights up, and after the control circuit 29 in FIG. 12, confirms no malfunction, the laser irradiation waiting condition is taken. In the waiting condition, when the foot switch 15 in FIG. 11 is activated, a laser beam with a wavelength of 970 nm is generated by the diode laser 21 and outputted from the tip portion of the optical fiber cable 2.

Furthermore, in another operation of the laser irradiation apparatus according to this embodiment, if setting the optical fiber cable selection switch 8 to the optical fiber cable 3, the lamp of the indicator 10 goes on, and the reflecting mirror 24 moves in a position to reflect the laser beam 22 so that the optical path selection causees the laser beam to use the optical fiber cable 3. During the irradiation by the optical fiber cable 3, the laser output mode, the output value and the irradiation time are displayed on the display section 14 and set to appropriate values through the output setting switch 13.

Since the diode laser 21 functions as an exciting light source for the solid state laser medium 72 (see FIG. 3) integrally placed at the tip portion of the optical fiber cable 3, the value for the laser output 76 (see FIG. 3) as a wavelength of 2.8 $\mu$m to be emitted from the solid state laser oscillating section 3a is displayed on the display section 14, and the control is performed by the control circuit 29 with respect to the output of the diode laser 21. The oscillation wavelength of the diode laser 21 is altered to 967 nm which causes the solid state laser medium 72 to generate a laser beam with a wavelength of 2.8 $\mu$m at high efficiency.

When the switch 12 is pushed down after the completion of the setting of the optical fiber cable selection switch 8 and the output setting switch 13, the lamp integral with the switch 12 turns on, and the control circuit 29 confirms no malfunction, thereafter gooing into the laser irradiation waiting condition. While in this waiting condition, if the foot switch 15 is activated, the solid state laser medium 72 is excited by the diode laser beam 22, so that the laser beam 76 with the wavelength of 2.8 $\mu$m is outputted from the tip portion of the optical fiber cable 3.

Moreover, in a different operation of the laser irradiation apparatus according to this embodiment, if the optical fiber cable selection switch 8 is set to the optical fiber cable 4, the lamp of the indicator 11 goes on, and the reflecting mirror 25 moves to a position to reflect the laser beam 22 so that the optical path selection selects the use of the optical fiber cable 4. At the irradiation by the optical fiber cable 4, the laser output mode, the output value and the irradiation time are displayed on the display section 14 and set to appropriate values through the output setting switch 13.

Since the diode laser 21 functions as an exciting light for the solid state laser medium 83 (see FIG. 4) integrally placed at the tip portion of the optical fiber cable 4, the value for the laser output (see FIG. 4) with a wavelength of 275.5 nm to be emitted from the wavelength converting section 4a is displayed on the display section 14. Control is performed by the control circuit 29 with respect to the output of the diode laser 21, and the oscillation wavelength of the diode laser 21 is altered to provide an output of 975 nm which can cause the solid state laser medium 83 generate a laser beam with a wavelength of 551 nm with the high efficiency.

When the switch 12 is pushed down after the completion of the setting of the optical fiber cable selection switch 8 and the output setting switch 13, the lamp integral with the switch 12 goes on, and the control circuit 29 confirms no malfunction, thereafter coming into the laser irradiation waiting condition. In this waiting condition, if foot switch 15 is activated, the solid state laser medium 83 is excited by the diode laser beam 22 so that the laser beam 84 with the wavelength of 551 nm is generated and the wavelength of the laser beam 84 is converted through the nonlinear optical crystal 85 to ½ the input wavelength, and the laser beam 86 with a wavelength of 275.5 nm is outputted from the tip portion of the optical fiber cable 4.

The connectors for making the connection of the optical fiber cables 2, 3, 4 to the laser irradiation apparatus 1 are respectively provided with the projections indicated at 19a, 19b, 19c in FIG. 6, the receptacles 5, 6, 7 in the laser irradiation apparatus 1 are respectively equipped with fitting sections corresponding to the projection sections 19a, 19b, 19c, and therefore, the optical fiber cables 2, 3, 4 are respectively exclusively connectable with the receptacles 5, 6, 7.

As described above, in the arrangements according to this invention, in a medical laser irradiation apparatus, at least two irradiation optical fiber cables including one having a solid state laser medium and/or a nonlinear optical crystal at their tip portions are used for outputting laser beams of a plurality of wavelengths capable of being transmitted in the quartz optical fiber, and therefore, it is possible to emit laser beams of at least two wavelengths, for example, in an ultraviolet region or in a wavelength region above 2.5 $\mu$m, which are hard to transmit in an quartz optical fiber, by the irradiation optical fiber cable tip portion.

Furthermore, since it is possible to use a relay optical fiber cable comprising a general-purpose quartz optical fiber, it is possible to shorten the length of the irradiation optical fiber cable. Further it is ease to conduct an unavoidable processing of treatment such as sterilization, and to set the length of the irradiation optical fiber cable to a length required for different medical equipment to be used together in a medical case.

Still further, mechanism is provided which identifies the above-mentioned two or more kinds of irradiation optical fiber cables, thus, it is possible to ensure the safe use of the laser irradiation apparatus without connecting erroneous irradiation optical fiber cables, and hence, the practical effects greatly improve, thus greatly contributing to a wider application of the medical laser irradiation apparatus.

Moreover, in the medical laser irradiation apparatus equipped with a diode laser light source, if two or more types of optical fiber cables including one having the solid state laser medium and/or the nonlinear optical crystal at their tip portions are used with one laser generating means, it is possible to generate laser beams with wavelengths corresponding to the types of optical fiber cables.

Besides, in addition to the change of the oscillation wavelength of the diode laser due to the change of the temperature, for example, it is also possible to employ an change means in which a grating mirror is placed within a resonator and is rotated.

The present invention is not limited to the above embodiments and various changes and modifications can be made within the spirit and scope of the present invention. Therefore, to apprise the public of the scope of the present invention the following claims are made.

What is claimed is:

1. A medical laser irradiation system including a laser irradiation apparatus and at least two irradiation optical fiber cables which have a solid state laser medium, or nonlinear optical crystal or quartz optical fiber respectively, each capable of selectively being coupled to said laser irradiation apparatus;

wherein one of said irradiation optical fiber cables comprises quartz optical fiber to be used as light guiding path, and said solid state laser medium or said nonlinear optical crystal which is set on a tip portion of said quartz optical fiber and is capable of generating a laser beam with a wavelength which is 300 nm or less, or 2.5µ or more;

wherein said laser irradiation apparatus is equipped with laser beam generating means capable of generating laser beams of a plurality of wavelengths which are transmittable through said quartz optical fibers, changing means for changing a wavelength of a laser beam to be outputted from said laser irradiation apparatus, so that, in accordance with a kind of said irradiation optical fiber cable connected to said laser irradiation apparatus, a laser beam with a wavelength suitable for excitation of said solid state laser medium or for wavelength conversion by said nonlinear optical crystal is guided into the interior of said irradiation optical fiber cable; and wherein laser beams of at least two wavelengths, which are 300 nm or less, or 2.5 µm or more, are emitted from the tip portion of said irradiation optical fiber cable.

2. A medical laser irradiation system according to claim 1, further comprising detecting means for detecting the kind of said irradiation optical fiber cable connected to said laser irradiation apparatus.

3. A medical laser irradiation system according to claim 1, wherein said laser beam generating means includes a diode laser.

4. A medical laser irradiation system according to claim 1, further comprising a relay optical fiber cable composed of quartz optical fiber, said relay optical fiber cable being provided between said laser irradiation apparatus and said irradiation optical fiber cable.

5. A medical laser irradiation system according to claim 4, further comprising detecting means for detecting the kind of said irradiation optical fiber cable connected to said relay optical fiber cable.

6. A medical laser irradiation system according to claim 1, wherein said laser generating means includes one laser light source and drive means for generating laser beams of a plurality of wavelengths from said laser light source.

7. A medical laser irradiation system according to claim 6, wherein said one laser light source is composed of a diode laser, and said drive means is equipped with temperature changing means for changing the temperature of said diode laser.

8. A medical laser irradiation system according to claim 7, wherein said temperature altering means includes a Peltier device and a current value altering circuit for changing the current to be supplied to said Peltier device.

9. A medical laser irradiation system according to claim 8, further comprising temperature detecting means for monitoring the temperature of said Peltier device.

10. A medical laser irradiation system according to claim 6, wherein said one laser light source is a titanium-sapphire laser.

11. A medical laser irradiation system according to claim 1, wherein said laser beam generating means is equipped with a plurality of laser light sources for generating laser beams having different wavelengths.

* * * * *